United States Patent [19]
Turner et al.

[11] Patent Number: 6,034,269
[45] Date of Patent: Mar. 7, 2000

[54] PROCESS FOR PRODUCING PURE CARBOXYLIC ACIDS

[75] Inventors: John Arthur Turner, North Yorkshire; Duncan Charles Woodcock, Warrington, both of United Kingdom

[73] Assignee: E. I. du Pont de Nemours and Company, Wilmington, Del.

[21] Appl. No.: 09/127,751

[22] Filed: Aug. 3, 1998

[51] Int. Cl.⁷ .......................... C07C 51/255; C07C 51/42
[52] U.S. Cl. ..................... 562/412; 562/414; 562/485; 562/486
[58] Field of Search .................... 562/414, 485, 562/486, 412

[56] References Cited

U.S. PATENT DOCUMENTS

| | | | |
|---|---|---|---|
| 3,507,913 | 4/1970 | Motoo et al. | 260/524 |
| 3,665,033 | 5/1972 | Ohlswager | 260/524 R |
| 4,892,970 | 1/1990 | Nowicki et al. | 22/413 |
| 5,110,984 | 5/1992 | Janulis | 562/487 |
| 5,175,355 | 12/1992 | Streich et al. | 562/485 |
| 5,376,350 | 12/1994 | Tenney et al. | 423/478 |
| 5,409,672 | 4/1995 | Cetinkaya | 422/189 |
| 5,840,965 | 11/1998 | Turner et al. | 562/412 |

FOREIGN PATENT DOCUMENTS

| | | | |
|---|---|---|---|
| 0 041 784 | 12/1981 | European Pat. Off. | C07C 63/26 |
| 1 574 651 | 9/1980 | United Kingdom | C07C 51/265 |

*Primary Examiner*—Rosalynd Keys
*Attorney, Agent, or Firm*—Charles E. Krukiel

[57] ABSTRACT

A process for producing pure carboxylic acids by catalytic liquid phase oxidation of a suitable precursor in a solvent in which the oxidation reaction is carried out in a plug flow reaction zone at a high solvent:precursor ratio and reaction conditions sufficient to maintain the pure acid in solution as it is formed, and product produced from such process.

5 Claims, No Drawings

PROCESS FOR PRODUCING PURE CARBOXYLIC ACIDS

BACKGROUND OF THE INVENTION

The present invention relates to an improved process for producing pure carboxylic acids by catalytic liquid phase oxidation of a suitable precursor in a solvent, and, more particularly, to a process for producing highly pure terephthalic acid according to such process by conducting the oxidation reaction in a plug flow reaction zone at a high solvent:precursor ratio, temperature and pressure sufficient to maintain the terephthalic acid in solution as it is formed. Thereafter, pure terephthalic acid is systematically crystallized from the resulting reaction medium and recovered as pure crystals without the need for separate purification.

Pure terephthalic acid, an important raw material used in the production of poly(ethylene terephthalate), i.e., PET, for conversion into fibers, films and containers, is commercially produced by purifying crude- or technical-grade terephthalic acid. Practically all technical-grade terephthalic acid is produced by catalytic, liquid phase air oxidation of paraxylene. Commercial processes use acetic acid as a solvent and a multivalent heavy metal or metals as catalyst. Cobalt and manganese are the most widely used heavy metal catalysts, and bromine is used as a renewable source of free radicals in the process.

Acetic acid, air (molecular oxygen), paraxylene and catalyst are fed continuously into an oxidation reactor that is maintained at from 175° C. to 225° C. and 1500–3000 kPa (i.e., 15–30 atm). The feed acetic acid:paraxylene ratio is typically less than 5:1. Air is added in amounts in excess of stoichiometric requirements to minimize formation of by-products. The oxidation reaction is exothermic, and heat is typically removed by allowing the acetic acid solvent to boil. The corresponding vapor is condensed and most of the condensate is refluxed to the reactor. Two moles of water are formed per mole of paraxylene reacted, and the residence time is typically 30 minutes to 2 hours, depending on the process.

The effluent from the reactor is a slurry of crude terephthalic acid crystals which are recovered by filtration, washed, dried and conveyed to storage. They are thereafter fed to a separate purification step. The main impurity is 4-carboxybenzaldehyde (4-CBA), which is incompletely oxidized paraxylene. Although the purity of crude-grade terephthalic acid is typically greater than 99%, it is not pure enough for the PET made from it to reach the required degree of polymerization.

SUMMARY OF THE INVENTION

The present invention is an improved continuous process for producing pure carboxylic acids by catalytic liquid phase oxidation of a suitable corresponding precursor in a solvent comprising an aliphatic carboxylic acid and optionally water which substantially reduces reactor residence time and provides for precipitation of pure acid crystals directly from the resulting reaction medium in a systematic, i.e., defined, crystallization sequence which is separate from the oxidation reaction. In the case of terephthalic acid, for example, the process of the invention eliminates the need for separate purification of crude TA crystals. The process comprises:

(a) forming a feed stream comprising solvent and oxidation catalyst at a pressure in the range of from 2,000 to 10,000 kPa;

(b) dissolving gaseous oxygen in the feed stream to achieve an oxygen concentration in the range of from 0.5% to 3.0% w/w and optionally preheating the feed stream to a temperature in the range of from 120° C. to 180° C.;

(c) continuously and simultaneously feeding the feed stream and a precursor to a plug flow reaction zone to form a reaction medium in which the solvent:precursor ratio is at least about 30:1 and the resulting carboxylic acid is maintained in solution as it is formed;

(d) systematically reducing the pressure of the reaction medium from step (c) while cooling it to a temperature in the range of from 120° C. to 180° C. thereby precipitating pure acid crystals to form a slurry of pure crystals in the reaction medium;

(e) optionally concentrating the slurry; and (f) recovering the pure acid crystals from the slurry.

The pure acid crystals can be recovered from the reaction medium, also referred to herein as "mother liquor", as a wet cake by filtration and washing, and then conveyed directly to a next reaction step, e.g., esterification, or the crystals can be dried and conveyed to storage.

According to another aspect of the invention, precipitation, i.e., crystallization, of the pure acid crystals from the reaction medium is accomplished in a defined sequence by (i) first reducing the pressure of the reaction medium to a value in the range of from 1,000 to 3,000 kPa whereby unreacted oxygen, water, acetic acid and volatile by-products, e.g., carbon oxides, vaporize, and the vapor is vented from the reaction medium, and thereafter (ii) reducing the pressure of the reaction medium in one or more additional steps to a value in the range of about 300 kPa while cooling the reaction medium to a temperature of about 150° C.

The present invention, according to another aspect, is a new composition of matter consisting essentially of substantially pure terephthalic acid in the form of discrete rhomboid crystals which are produced by the process of:

(a) forming a feed stream comprising acetic acid and an oxidation catalyst at a pressure in the range of from 2,000 to 10,000 kPa;

(b) dissolving gaseous oxygen in the feed stream to achieve an oxygen concentration in the range of from 0.5% to 3.0% w/w and optionally preheating the feed stream to a temperature in the range of from 120° C. to 180° C.;

(c) continuously and simultaneously feeding the feed stream and paraxylene to a plug flow reaction zone to form terephthalic acid within a reaction medium in which the acetic acid:paraxylene ratio is at least about 30:1 and the terephthalic acid thus formed is maintained in solution;

(d) systematically reducing the pressure of the reaction medium from step (c) while cooling it to a temperature in the range of from 120° C. to 180° C. thereby precipitating substantially pure terephthalic acid crystals to form a slurry;

(e) optionally concentrating the slurry; and (f) recovering the substantially pure terephthalic acid crystals from the slurry. Pure terephthalic acid crystals produced according to the invention are distinctly angular, e.g., rhomboid, in structure, and thereby differ from TA crystals produced according to the prior art, which tend to be rounded agglomerates of many smaller crystals.

The process of the invention results in the production of highly pure carboxylic acid crystals from a single stage plug flow oxidation reaction sequence, including crystallization and product recovery, i.e., without the need for a separate additional purification stage.

DETAILED DESCRIPTION

The present invention is an improved continuous process for catalytic liquid phase oxidation of a suitable precursor, such as paraxylene, in the presence of an aliphatic carboxylic acid solvent, particularly acetic acid, to produce highly pure carboxylic acid. In the case of terephthalic acid (TA), the pure crystals are in the form of discrete distinctly angular crystals of a rhomboid structure as distinguished from TA acid crystals produced according to known oxidation/purification processes. As used herein in describing carboxylic acid crystals produced according to the process of the invention, the terms "pure", "highly pure", and "substantially pure" are used interchangeably and mean such acid crystals having a purity of at least 99.5% by wt., although the purity can be as high as 99.9% by wt. and even higher, e.g., 99.95% by wt.

The process will be described as it relates to the production of highly pure terephthalic acid, although it is applicable to the production of a range of pure benzenepolycarboxylic acids, such as, phthalic acid, isophthalic acid, etc., and mixtures thereof. The process is carried out by first forming a feed stream comprising solvent, i.e., an aliphatic carboxylic acid, which is typically acetic acid, or a non-aliphatic organic solvent such as benzoic acid, and an oxidation catalyst at an elevated pressure in the range of from 2,000 kPa up to 10,000 kPa. In practice, the feed stream will usually contain some amount of water. The term "solvent", as used in describing the process of the invention, therefore, means the total amount of (i) water, if present, which can be at a concentration of from 3% by wt. up to as high as 30% by wt., and (ii) aliphatic carboxylic acid, or non-aliphatic organic acid.

Molecular oxygen is dissolved in the feed stream to achieve a concentration of dissolved oxygen of from 0.5% to 3.0% w/w, and the feed stream can then be heated to a temperature in the range of from 120° C. up to 180° C. before being introduced into the reaction zone. The source of oxygen can be pure oxygen, air, or any convenient oxygen-containing gas.

In practice, the feed stream is fed into a plug flow reactor simultaneously and continuously with paraxylene and catalyst to thereby form a reaction medium in which the resulting solvent:paraxylene ratio is at least about 30:1, although the solvent:paraxylene ratio can be as high as 200:1 with the process achieving satisfactory results. In a preferred embodiment, the solvent:paraxyene ratio is in the range of 65:1.

The process is carried out in the presence of an oxidation catalyst which can be homogeneous or heterogeneous and selected from one or more heavy metal compounds, such as, for example, cobalt and/or manganese compounds. In addition, the catalyst can also include an oxidation promoter such as bromine or acetaldehyde. The selection of catalyst and oxidation promoter and their use and handling throughout the process according to the invention is within conventional practice. The catalyst/oxidation promoter components are added to the feed stream in liquid form as a solution before the feed stream is introduced into the reaction zone, and they largely remain in solution throughout the process.

The term "plug flow reactor" is used herein to define a typically tubular reaction zone in which radial mixing of the reactants occurs as they flow through the tube or conduit. The invention, however, is intended to embrace any reactor configuration which approximates a plug flow reaction zone of a type suitable for carrying out the oxidation reaction according to the process of the invention, i.e., carrying out the oxidation reaction in a non-boiling liquid phase. The residence time of the reaction medium within the reaction zone is relatively short, i.e., on the order of 5 minutes or less, which takes into account the discovery that the reaction is selective and proceeds very rapidly under the process conditions of the invention. In practice, it has been observed that the oxidation reaction under plug flow runs to desired conversion in from 0.5 to 2.5 minutes.

The oxidation reaction is exothermic to the extent of $12.6 \times 10^6$ J/kg of paraxylene reacted. Typically, this heat has been removed by allowing the acetic acid solvent to boil, with the resulting vapor being condensed and the condensate in varying amounts being refluxed to the reactor. According to the present invention, however, the choice of solvent, solvent:precursor ratio, temperature and pressure cooperate to maintain the reaction medium, particularly oxygen and TA, in a non-boiling liquid phase as the reaction medium passes through the plug flow reaction zone. Furthermore, in operation the heat of reaction need not necessarily be removed from the reaction zone.

The pure TA is recovered from the reaction medium in a crystallization process which is separate from the plug flow oxidation reaction. Crystallization involves systematically reducing the pressure and temperature of the reaction medium whereby TA precipitates from the reaction medium as substantially pure crystals while impurities and other reaction by-products remain in solution. The reaction medium exits the plug flow reaction zone at a temperature in the range of from 180° C. to as high as 250° C. and a pressure in the range of from 2,000 kPa to 10,000 kPa and is passed to a separate crystallization step. Crystallization can be accomplished by reducing the pressure of the reaction medium to about 300 kPa in a single step or in several graduated steps while reducing the temperature to a value in the range of about 150° C.

In a preferred embodiment of the invention, crystallization of the pure TA crystals is accomplished in two basic stages. In a first stage, the pressure of the reaction medium is reduced to a value in the range of from 1,000 to 3,000 kPa, e.g., 2,000 kPa, whereby unreacted oxygen, water, acetic acid and volatile by-products, e.g., carbon oxides, vaporize and the vapor is vented from the reaction medium. Thereafter, in a second stage, the pressure of the reaction medium is further reduced in one or more additional steps while the reaction medium is cooled to around 150° C. Pressure reduction can be accomplished by any suitable means, such as, for example, by passing the reaction medium through a pressure reducing valve or a liquid turbine.

Pure TA crystals precipitate from the reaction medium and form a dilute slurry of from 1% to 6% w/w concentration. It has been discovered that by reducing the temperature of the reaction medium according to the present process to a value in the range of 150° C. for crystallization, primary impurities, such as 4-CBA and undesirable color bodies, which would otherwise precipitate with the TA, remain in solution. Thus, it is possible according to the invention to produce pure TA crystals via catalytic liquid phase oxidation of paraxylene without the need for a separate purification step.

For economy in operation, the dilute slurry can be thickened, i.e., concentrated, by any suitable means to a higher acid crystal concentration up to about 60% w/w. Thereafter, the pure TA crystals can be recovered from the slurry by filtration, washed, and optionally dried and sent to storage. The reaction medium which remains after pure TA crystals are recovered, i.e., the mother liquor, can be recycled and fed as a component of the feed stream to the oxidation reaction.

In practice, the feed stream for operating the process on a continuous basis will comprise recycled mother liquor which is supplemented with fresh aliphatic carboxylic acid (e.g., acetic acid) and fresh liquid catalyst make-up to account for chemical and physical losses from the original feed stream. The feed stream will be pressurized and oxygenated, and then fed simultaneously with liquid paraxylene into the plug flow reaction zone at an inlet temperature of about 120° C. to 150° C. and elevated pressure to achieve a solvent:paraxylene ratio of about 65:1 for the resulting reaction medium with the result that the reaction proceeds rapidly (i.e., from 0.5 to 2.5 minutes reactor residence time) without boiling, and TA remains in solution as it is formed. Although the reaction can be adiabatic, cooling means can be employed to recover and reuse heat directly from the reaction.

The invention will now be described with reference to the following examples.

EXAMPLES

Example 1
Plug Flow Reactor Oxidations

Experiments were performed using a plug flow reactor system comprising two feed vessels, a reaction coil and two product collection vessels. Simultaneous flow from the feed vessels through the reaction coil into either one of the product collection vessels was established by differential gas pressure and appropriate valve operations.

The first vessel was charged with a known compositon of paraxylene in acetic acid/water solvent. The second feed vessel was charged with a known composition of catalyst in acetic acid/water solvent. Air was introduced into both feed vessels, through dip pipes, at a pressure to ensure that the desired amount of oxygen (in excess of the stoichiometric paraxylene requirement) went into solution. The feed vessels and reaction coil were immersed in an oil bath to preheat the feeds to the required reaction temperature. Simultaneous flow from the feed vessels through the reaction coil was then established into the first product collection vessel labeled as "off spec". After a predetermined time, the product stream from the reaction coil was switched to the second product collection vessel. After a further predetermined time, the product stream was switched back to the "off-spec" collection vessel. At the end of the experiment, all vessels were cooled, vented, washed out and drained. The solid and liquid contents of the sample product collection vessel were recovered, weighed and analyzed, and the composition of the reaction solution leaving the reaction coil was calculated.

In Table 1, the concentrations of the TA precursors paratolualdehyde (ptolald), paratoluic acid (ptol) and 4-carboxybenzaldehyde (4-CBA) are reported for experiments where the reaction residence time was varied. At this scale, the reactions ran under nearly isothermal conditions, close to the oil bath temperature of 210° C. throughout.

The Examples demonstrate the effect of residence time on precursor concentrations. At 4.86 minutes residence time, single pass paraxylene conversion to TA was greater than 99.5% (precursors less than 0.5% of feed paraxylene). At 1.28 minutes residence time, single pass paraxylene conversion to TA fell to about 84%. Significantly, however, paraxylene conversion to 4-CBA (the intermediate that tends to co-precipitate with TA in conventional processes) is of the order of 1% or below throughout. High single pass conversion of paraxylene to TA is not essential to the process so long as the 4-CBA concentration in the reaction stream leaving the reactor is low. During the crystallization step, TA precursors substantially remain in solution in the reaction medium, i.e., dissolved in the mother liquor, and thereby they can be recycled to the plug flow oxidation reactor.

Table 1: Plug Flow Reactor Oxidation Results

In all experiments, the following parameters were fixed (all compositions are w/w);

Solvent:water 5%, acetic acid 95%
Paraxylene:0.5% w/w (200:1 solvent:paraxylene ratio)
Catalyst:Co 632 ppm, Mn 632 ppm, Br 1264 ppm+Zr 96 ppm
Oil Bath Temperature:210° C.

| Example | Reaction Time (min) | Reactor Solution (ppm w/w) | | |
|---|---|---|---|---|
| | | ptolald | ptol | 4 CBA |
| 1 | 1.28 | 228 | 687 | 6 |
| 2 | 1.78 | 55 | 411 | 51 |
| 3 | 2.28 | 132 | 312 | 42 |
| 4 | 2.31 | 99 | 192 | 38 |
| 5 | 3.29 | 15 | 82 | 6 |
| 6 | 4.86 | 1.7 | 27 | <0.1 |

Example 2
Crystallization

A solution of 2% w/w terephthalic acid (TA), 125 ppm 4-CBA, 175 ppm ptol and other oxidation intermediates in 5% w/w water, 95% w/w acetic acid solvent was prepared at elevated temperature (210° C.) and at a pressure sufficiently high to maintain a liquid phase. The solution was passed, continuously, through a pressure reducing valve into a crystallizer vessel whose pressure and temperature was controlled such that TA precipitated from solution. The slurry produced in the crystallizer was passed forward to further crystallization vessels in which the pressure and temperature were systematically reduced to ambient conditions, and further TA precipitated.

During the course of the experiment, crystals from the first crystallizer (Hot Filtered TA) were recovered and analyzed for 4-CBA and paratoluic acid (ptol) content and median particle size (using a Coulter LS230 Laser Diffraction psd analyzer). Crystals from the downstream vessels (Cold Filtered TA) were also recovered and analyzed for reference purposes.

In Table 2, the Hot Filtered TA, 4-CBA and ptol contents and median particle sizes are reported for experiments where the first crystallizer temperature, residence time and stirrer speed were varied. For reference, one analysis of Cold Filtered TA is also included. Examples 7, 8 and 9 show that, in the Hot Filtered TA, 4-CBA and ptol contents fell as the filtration temperature was reduced from 196 to 148° C. The data also shows that median particle size inceases with reducing temperature. In a separate experiment, Examples 10 and 11 show that, in the Hot Filtered TA, reduction in filtration temperature from 151° to 126° C. causes 4-CBA level to increase, while ptol level and median particle size decline.

When viewed together, Examples 7 through 11 indicate an optimum crystallizer temperature, with respect collectively to intermediates incorporation and median particle size, in the region 140° to 160° C., particularly around 150° C.

Examples 12 and 13 show that increasing first crystallizer residence time from 9 to 18 minutes benefits both intermediates incorporation and median particle size. Examples 14 and 15, when viewed alongside Example 9, show that increasing first crystallizer agitator speed, from 270 to 1000 rpm, does not have a strong influence on median particle size, but tends to reduce intermediates incorporation.

Table 2 Crystallization Experiments Results

In all experiments the following parameters were fixed (all compositions are w/w);

Solvent:water 5%, acetic acid 95%

Feed Solution Aromatics:TA 2%, 4CBA 125 ppm, ptol 175 ppm

Feed Solution Temperature:210° C.

| Ex. | First Cryst. Res. Time (min) | First Cryst. Stirrer Speed (rpm) | First Cryst. Temp. (° C.) | 4CBA Content (ppm) | ptol Content (ppm) | Median Particle Size (micron) |
|---|---|---|---|---|---|---|
| 7 | 12 | 1,000 | 196 | 2,360 | 345 | 59 |
| 8 | 12 | 1,000 | 176 | 1,040 | 218 | 114 |
| 9 | 12 | 1,000 | 148 | 670 | 89 | 134 |
| 10 | 18 | 1,500 | 151 | 710 | 138 | 96 |
| 11 | 18 | 1,500 | 126 | 1,060 | 117 | 86 |
| 12 | 18 | 1,000 | 173 | 980 | 150 | 106 |
| 13 | 9 | 1,000 | 179 | 1,140 | 217 | 96 |
| 14 | 12 | 270 | 152 | 930 | 123 | 139 |
| 15 | 12 | 500 | 150 | 790 | 106 | 135 |
| Ref. | 12 | 1,000 | 148 | 2,340 (Cold Filter) | 281 (Cold Filter) | 102 (Cold Filter) |

What is claimed is:

1. A process for producing a pure carboxylic acid by catalytic liquid phase oxidation of a corresponding precursor in a solvent selected from an aliphatic carboxylic acid or a non-aliphatic organic acid and optionally including water which comprises:

(a) forming a feed stream comprising solvent and oxidation catalyst at a pressure in the range of from 2,000 to 10,000 kPa;

(b) dissolving gaseous oxygen in the feed stream to achieve an oxygen concentration in the range of from 0.5% to 3.0% w/w and optionally preheating the feed stream to a temperature in the range of from 120° C. to 180° C.;

(c) continuously and simultaneously feeding the feed stream and said precursor to a plug flow reaction zone to form a reaction medium in which the solvent:precursor ratio is at least about 30:1 and resulting carboxylic acid is maintained in solution as it is formed;

(d) systematically reducing the pressure of the reaction medium from step (c) while cooling it to a temperature in the range of from 120° C. to 180° C. thereby precipitating carboxylic acid crystals to form a slurry;

(e) optionally concentrating the slurry; and (f) recovering the carboxylic acid crystals from the slurry.

2. The process of claim 1 in which systematically reducing the pressure of the reaction medium from step (c) is accomplished by (i) first reducing the pressure of the reaction medium to a value in the range of from 1,000 to 3,000 kPa whereby unreacted oxygen, water, precursor and volatile by-products vaporize and the vapor is vented from the reaction medium, and thereafter (ii) reducing the pressure of the reaction medium in one or more additional steps to a value in the range of 300 kPa while cooling the reaction medium to a temperature of about 150° C.

3. The process of claim 1 or claim 2 which includes the additional step of recycling the reaction medium remaining from step (f) as a component of the feed stream to the reactor.

4. A process for producing pure terephthalic acid by catalytic liquid phase oxidation of paraxylene in a solvent selected from an aliphatic carboxylic acid and optionally including water which comprises:

(a) forming a feed stream comprising solvent and oxidation catalyst at a pressure in the range of from 2,000 to 10,000 kPa;

(b) dissolving gaseous oxygen in the feed stream to achieve an oxygen concentration in the range of from 0.5% to 3.0% w/w and optionally preheating the feed stream to a temperature in the range of from 120° C. to 180° C.;

(c) continuously and simultaneously feeding the feed stream and said paraxylene to a plug flow reaction zone to form terephthalic acid in a reaction medium in which the solvent:paraxylene ratio is at least about 30:1 and the terephthalic acid is maintained in solution as it is formed;

(d) systematically reducing the pressure of the reaction medium from step (c) while cooling it to a temperature in the range of from 120° C. to 180° C. thereby precipitating terephthalic acid crystals to form a slurry;

(e) optionally concentrating the slurry; and (f) recovering the terephthalic acid crystals from the slurry.

5. The process of claim 4 in which systematically reducing the pressure of the reaction medium from step (c) is accomplished by (i) first reducing the pressure of the reaction medium to a value in the range of from 1,000 to 3,000 kPa whereby unreacted oxygen, water, precursor and volatile by-products vaporize and the vapor is vented from the reaction medium, and thereafter (ii) reducing the pressure of the reaction medium in one or more additional steps to a value in the range of 300 kPa while cooling the reaction medium to a temperature of about 150° C., and the process includes the additional step of recycling the reaction medium remaining from step (f) as a component of the feed stream to the reactor.

* * * * *